United States Patent [19]

Nitta et al.

[11] 4,311,646
[45] Jan. 19, 1982

[54] PROCESS FOR THE PREPARATION OF 4,6-DIEN-3-ONE STEROIDS

[75] Inventors: Issei Nitta, Machida; Toshio Haruyama, Sagamihara; Shinya Inoue, Yamato, all of Japan

[73] Assignee: Mitsubishi Chemical Industries Limited, Tokyo, Japan

[21] Appl. No.: 190,223

[22] Filed: Sep. 24, 1980

[30] Foreign Application Priority Data

Oct. 12, 1979 [JP] Japan .................................. 54-131511

[51] Int. Cl.$^3$ .............................................. C07J 7/00
[52] U.S. Cl. .................................................. 260/397.4
[58] Field of Search ............. 260/397.3, 397.4, 397.45

[56] References Cited

FOREIGN PATENT DOCUMENTS 958515  5/1964  United Kingdom ........... 260/397.45
1226356 3/1971  United Kingdom ........... 260/397.45

Primary Examiner—Elbert L. Roberts
Attorney, Agent, or Firm—Oblon, Fisher, Spivak, McClelland & Maier

[57] ABSTRACT

A 4,6-dien-3-one steroid is produced by brominating an enolic ether of a 4-en-3-one steroid in a water-containing organic solvent which is substantially free from acetic acid and sodium acetate to give a 6-bromosteroid and then dehydrobrominating the 6-bromosteroid in a medium which contains dimethylformamide or N-methylpyrrolidone and 1 to 9% by volume of water.

8 Claims, No Drawings

PROCESS FOR THE PREPARATION OF 4,6-DIEN-3-ONE STEROIDS

BACKGROUND OF THE INVENTION

1. Field of the Invention

This invention relates to a process for the preparation of 4,6-dien-3-one type steroids, and more particularly to an improved process for the preparation of 4,6-dien-3-one steroids by dehydrobromination of the corresponding steroid containing a bromine atom at the 6-position as a substituent.

4,6-Dien-3-one steroids are very important due to their pharmacological activity. Such steroids are exemplified by many steroids including, for example, cyproterone acetate, chlormadinone acetate, dydrogesterone, megesterol, melengesterol, medrogestone and canrenone.

Among the above-exemplified steroids, the first six steroids are active progestins and caurenone is useful as an intermediate for spironolactone which is an antialdosteronic diuretic and hypotensive. Accordingly it is desired to develop a process for preparing 4,6-dien-3-one steroids economically.

2. Description of the Prior Art

It is well known in the art that 4,6-diene-3-one steroids can be advantageously prepared by enolating a 4-en-3-one steroid at the 3-position carbon atom to give an enolic ether having partial structural formula (I) at the 3,4,5,6-position of rings A and B of the steroid:

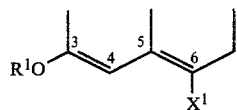

wherein $X^1$ is hydrogen, methyl, fluorine, chlorine or bromine and $R^1$ is an alkyl having 1 to 3 carbon atoms, then brominating the enolic ether at the 6-position carbon atom to give a 6-bromosteroid having partial structural formula (II) at the same position:

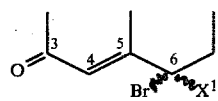

wherein $X^1$ is as defined above and one of $X^1$ and Br is in the α-configuration and the other is in the β-configuration, and dehydrobrominating the resulting 6-bromosteroid.

Now the above-mentioned prior-art process is described in detail. The enolic ether having partial formula (I) is brominated with a brominating agent capable of providing a positive bromine ion such as N-bromosuccinimide, N-dibromodimethylhydantoin, N-dibromobenzenesulfonamide or N-bromoacetamide in acetone solvent in the presence of sodium acetate, acetic acid and water. The resulting reaction mixture is poured onto a large amount of ice-water and the precipitate is collected by filtration and dried to isolate a crude 6-bromosteroid having partial formula (II).

Alternatively, the crude 6-bromosteroid may be isolated by solvent extraction, washing with water and phase separation to remove acetic acid and sodium acetate followed by evaporation of the solvent. The 6-bromosteroid is then subjected to dehydrobromination to give the desired 4,6-dien-3-one steroid having partial formula (III) at the same position:

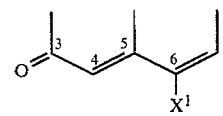

wherein $X^1$ is as defined above. The dehydrobromination is effected by dissolving the 6-bromosteroid in an aprotic solvent such as dimethylformamide or N-methylpyrrolidone and heating the solution at 100° C. or above in the presence of a lithium halide such as lithium bromide and an inorganic carbonate such as lithium carbonate or calcium carbonate, or by heating the 6-bromosteroid in a tertiary organic amine such as pyridine, collidine or dimethylaniline. In general, the former dehydrobromination technique employing lithium bromide is superior to the latter.

Upon our detailed study on the above-mentioned bromination-dehydrobromination process, it has been found that the 6-bromosteroids having partial formula (II) are so unstable that when they are in solution their degradation proceeds: even at room temperature and that their crude products precipitated out of an aqueous system can be recovered in a stable form only by lyophilization. The instability of steroid 6,6-dihalides is also apparent from Japanese Patent Laid-Open No. 24666/1968 which indicates that the yields of 4,6-dien-3-one steroids do not exceed 50% even in careful laboratory-scale experiments.

Thus, if the 6-bromosteroids having partial formula (II) is unstable, the bromination-dehydrobromination process can not be applied to commercial operation.

SUMMARY OF THE INVENTION

Upon extensive investigation, it has now been found that a 4,6-dien-3-one steroids having the above partial formula (III) can be prepared in good yield by adding dehydrobrominating reagents directly to the reaction mixture from the bromination step without isolating a 6-bromosteroid having partial formula (II) and by immediately conducting dehydrobromination reaction.

DETAILED DESCRIPTION OF THE PREFERED EMBODIMENTS

In the prior art process, the bromination step is carried out in the presence of acetic acid, sodium acetate and water, as previously mentioned. However, it has been found that when the reaction mixture from the bromination step is directly subjected to dehydrobromination with no working-up procedure, the dehydrobromination reaction is significantly adversely affected by acetic acid, sodium acetate and water. More specifically, acetic acid neutralizes a tertiary amine which may be used as a dehydrobrominating reagent or cause decomposition of a carbonate which may be used in combination with a lithium halide. In addition, acetic acid, sodium acetate and water can substitute for the bromine atom of a 6-bromosteroid, thereby giving undesirable solvolysis products and significantly decreasing the yield of a desired 4,6-dien-3-one steroid.

We have succeeded in obtaining a 6-bromosteroid having partial formula (II) in good yield without using acetic acid and sodium acetate which were considered as essential in the prior-art bromination of an enolic ether steroid having partial formula (I) into a 6-bromosteroid having partial formula (II), whereby one of difficulties has been overcome.

A second difficulty is the presence of water. From the standpoint of stoichiometry water is essential for the bromination reaction and it is impossible to effect this reaction in the absence of water. In fact, the yield of a 6-bromosteroid is significantly decreased when the water content of the reaction system is not greater than 1.5% of the solvent or not greater than twice the molar amount of the enolic ether.

On the other hand, the dehydrobromination reaction is usually carried out under water-free conditions since undesirable side reactions may occur together with dehydrobromination in the presence of water. If the reaction is carried out by direct addition of dehydrobrominating reagents to the reaction mixture from the brominating reaction, it is expected that some water which is essential for the bromination step is enevitably incorporated in the subsequent dehydrobromination step. Such incorporation of water was considered unfavorable for commercial operation.

Upon our restudy about adverse effect of water on the dehydrobromination step, it has been found that the presence of water in an amount exceeding 10% by volume does bring about a significantly decreased yield. However, unexpectedly it has also been found that a satisfactorily high yield can be attained even in the presence of water if the amount of water is not greater than 9% by volume, preferably not greater than 7%. In addition, it has been found unexpectedly that the yield is decreased again in the absence of water and that at least 1.0% by volume, preferably at least 1.5% of water is rather necessary to attain a satisfactory yield. In accordance with the present invention, the dehydrobromination is carried out, on the basis of the above discovery, in a solvent system containing 1 to 9% by volume, preferably 1.5 to 7% and more preferably 2 to 5% of water whereby the bromination reaction can be immediately followed by the dehydrobromination reaction. In accordance with the improved process of the present invention, the desired 4,6-dien-3-one steroid can be obtained in high yield, e.g., approximately 90%, even in the case where the intermediate 6-bromosteroid having partial formula (II) is unstable.

Even in the case where the 6-bromosteroid having partial formula (II) is stable, the present process is of great significance in commercial operation in that it is more simple and hence contributes to an improved productivity.

Now the present improved process is described in detail. The steroids having partial formula (I) include those represented by the formula:

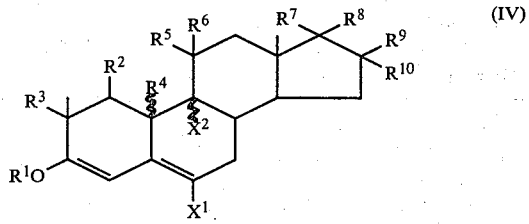

(IV)

wherein $X^1$ and $R^1$ is as defined in formua (I); $X^2$ is hydrogen, fluorine or chlorine; $R^2$ and $R^3$ are each hydrogen or, taken together, may represent a 1α, 2α-methylene group; $R^4$ is hydrogen or methyl; $R^5$ and $R^6$ are each hydrogen or hydroxyl group provided that at least one of $R^5$ and $R^6$ is hydrogen, or $R^5$ and $R^6$, taken together, may represent oxygen atom; $R^7$ and $R^8$ are a combination of hydrogen and hydroxyl, hydrogen and acyloxy, hydrogen and acetyl, hydrogen and acetoxyacetyl, hydroxyl and acetyl, hydroxyl and acetoxyacetyl or methyl and acetyl or $R^7$ and $R^8$, taken together, may form 4-oxa-3-oxo-1,4-butene group; $R^9$ and $R^{10}$ are a combination of hydrogen and methyl, hydrogen and ethyl or hydrogen and hydroxyl or $R^9$ and $R^{10}$, taken together, may represent a methylene group; and $X^2$ and $R^4$ may be in either the α- or β-configuration.

Among others, particularly when $X^1$ is methyl, fluorine or chlorine, the resulting intermediate 6-bromosteroid having partial formula (II) is unstable so that the present process is extremely valuable in such case.

$R^1$ is an alkyl such as methyl, ethyl or propyl and usually $R^1$ is methyl or ethyl.

The enolic ether steroid having partial formula (I) can be readily obtained in a manner known per se from the corresponding 4-en-3-one steroid by reaction with an orthoformate such as methyl orthoformate, ethyl orthoformate or propyl orthoformate in the presence of an acid catalyst such as p-toluenesulfonic acid.

The first step, i.e., bromination reaction, is effected by reacting the enolic ether with a brominating agent capable of providing a positive bromine ion such as N-bromosuccinimide, N-bromoacetamide, N-dibromodimethylhydantoin or N-dibromobenzenesulfonamide in an organic solvent in the presence of water.

Various solvents can be used, but it is preferred that the solvent be water-soluble and do not possess a nucleophilic property which enables the solvent to replace a halogen atom or the like. With a nucleophilic solvent such as an alcohol, even though the bromination reaction proceeds successfully, an undesirable solvolytic substitution product may be unfavorably formed during the subsequent dehydrobromination reaction which is carried out immediately in accordance with the present process. Preferred solvents include aliphatic ketones such as acetone, cyclic ethers such as tetrahydrofuran and dioxane, dimethylformamide, dimethyl sulfoxide and the like. Most preferred are acetone and tetrahydrofuran.

The amount of water is very important in the present invention. If no or little water is present, either the bromination reaction does not proceed or side reactions are induced significantly.

Usually, it is necessary that water be present in an amount of at least 2-times, preferably at least 3-times and more preferably at least 5-times the molar amount of the enolic ether having partial formula (I). However, if the amount of water is excessively large, for example, equal to the volume of the organic solvent, the solubility of the enolic ether having partial formula (I) is unfavorably so decreased that a satisfactory conversion into the 6-bromosteroid cannot be attained.

On the other hand, it is also necessary to keep the amount of water as small as possible since in the present process the bromination reaction is directly followed by the dehydrobromination.

It is usually preferable to use 2 to 22 moles of water, more preferably 3.5 to 16.5 moles of water per mole of the enolic ether having partial formula (I).

In the practice of the process of the present invention, no acetic acid nor sodium acetate is used. In the conventional process, acetic acid is usually employed for its promotor-like action as a proton source in the release of a positive bromine ion from a brominating agent such as N-bromosuccinimide, while sodium acetate is used in order to neutralize hydrobromic acid formed by a side reaction and keep constant the pH of the reaction mixture by buffering action.

The amount of the brominating agent used is within the range of from 1.05 to 2 moles, preferably from 1.05 to 1.5 moles and more preferably from 1.05 to 1.3 moles per mole of the enolic ether having partial formula (I). The reaction temperature is usually from $-10°$ to $50°$ C., preferably from $0°$ to $30°$ C.

The subsequent dehydrobromination reaction is carried out by adding dimethylformamide or N-methylpyrrolidone to the reaction mixture from the bromination. A lithium halide such as lithium chloride or lithium bromide and a carbonate such as lithium carbonate or calcium carbonate are then added and the mixture is heated.

The solvent to be added in this step is most preferably dimethylformamide and it is added in an amount of at least one-third, preferably at least one-half the volume of the solvent used in the bromination step. There is no upper limit of the amount of dimethylformamide or N-methylpyrrolidone and the more, the better. However, from the viewpoint of economics, such solvent is preferably used in an amount of not greater than 10-times the volume of the solvent used in the bromination step. In the present invention, the water content is critical. The amount of water present in the dehydrobromination step corresponds to the remainder of the water supplied to the bromination step from which the water consumed during the bromination reaction is subtracted. In the dehydrobromination step, the water content must be adjusted to 1 to 9% by volume, preferably 1.5 to 7% and more preferably 2 to 5% based on the total volume of solvents by controlling the amount of the added solvent.

The lithium halides include lithium chloride, lithium bromide, etc., and lithium bromide is preferred. They are used generally in an amount of at least 0.1 mole, preferably 0.3 to 3 moles per mole of the enolic ether. The carbonate is used in order to neutralize hydrobromic acid which is formed with the progress of the reaction. Suitable carbonates are lithium carbonate and calcium carbonate and they are used in an amount of 1 to 5 moles, preferably 1.5 to 3 moles per mole of the enolic ether.

The reaction temperature ranges from $50°$ to $150°$ C., preferably from $60°$ to $120°$ C.

Having generally described this invention, a more complete understanding can be obtained by reference to certain examples and comparative examples which are provided herein for purpose of illustration only and are not intended to be limiting in any manner.

EXAMPLE 1

In 20.0 ml of acetone and 0.80 ml of water is suspended 3.073 g of 6-chloro-3-ethoxy-17α-hydroxypregna-3,5-dien-20-one 17-acetate and cooled to $3°$ to $5°$ C. Then 1.304 g of N-bromosuccinimide is added and the mixture is stirred for 30 minutes.

To the resulting reaction mixture are added 10.0 ml of dimethylformamide, 1.123 g of lithium bromide hydrate and 1.108 g of lithium carbonate and the mixture is heated on an oil bath at $80°$ C. for 2.0 hours with stirring.

Upon cooling of the reaction mixture, 100 ml of water is added under stirring and the precipitated crystals are collected by filtration and dried to give 3.159 g of crude chlormadinone acetate.

The liquid-chromatographic analysis shows 87.8% yield of chlormadinone acetate.

The crude product is crystallized from methanol to give 2.26 g of crystals (m.p. 206.5° to 207.8° C.), which are recrystallized from methanol to give 2.03 g of purified chlormadinone acetate, m.p. 210.8° to 213.0° C.

Referential Examples 1 to 4

To 12.13 g of 6-chloro-3-methoxy-17α-hydroxypregna-3,5-dien-20-one 17-acetate are added 240 ml of acetone, 16 ml of acetic acid, 4.4 g of sodium acetate and 40.0 ml of water and cooled on an ice-water bath. Then 5.75 g of N-bromosuccinimide is added and stirred for 1.0 hour.

The reaction mixture is poured onto 2,500 ml of ice water and the precipitated crystals are collected by filtration and lyophilized to give 13.49 g of 6-chloro-6-bromo-17α-hydroxyprogesterone 17-acetate as pale yellow crystals.

To 1.579 g of the obtained 6-chloro-6-bromo-17α-hydroxyprogesterone 17-acetate are added 15.0 ml of a solution of lithium bromide in dimethylformamide (prepared by dissolving 2.806 g of anhydrous lithium bromide in 100 ml of dimethylformamide), 0.33 g of lithium carbonate and a given amount of water and the mixture is heated on an oil bath at 80° C. for 0.5 hour with stirring.

After cooling of the reaction mixture, 500 ml of water is added and the mixture is extracted with 2×50 ml of chloroform. The combined chloroform layers are washed with water and dried over magnesium sulfate and the magnesium sulfate is filtered off. The concentration of chlormadinone acetate in the remaining chloroform solution is determined by liquid chromatography. The yields of chlormadinone acetate obtained in the cases where the amounts of water added in the dehydrobromination step are 0, 0.30, 0.7 and 1.5 ml are as follows:

| Referential Example No. | $H_2O$ ml | $H_2O$ Vol. %* | Yield of Chlormadinone Acetate |
| --- | --- | --- | --- |
| 1 | 0 | 0 | 63.1% |
| 2 | 0.30 | 2.0 | 83.5% |
| 3 | 0.70 | 4.7 | 84.9% |
| 4 | 1.5 | 10.0 | 68.2% |

*($H_2O$ ml/DMF ml) × 100
DMF = Dimethylformamide

EXAMPLE 2 and Comparative Examples 1 and 2

The procedure of Example 1 is repeated except that the amount of water is changed from 0.8 ml to 1.5 ml (Example 2), 0 ml (Comparative Example 1) and 3.0 ml (Comparative Example 2). The yields of chlormadinone acetate are as follows:

| | $H_2O$ ml | $H_2O$ Vol. % | Yield of Chlormadinone Acetate |
| --- | --- | --- | --- |
| Comp. Ex. 1 | 0 | 0 | 5.0% |
| Example 1 | 0.80 | 2.7 | 87.8% |
| Example 2 | 1.50 | 5.0 | 85.8% |
| Comp. Ex. 2 | 3.00 | 10.0 | 59.1% |

*[$H_2O$ ml/(Acetone + DMF) ml × 100

The solvents present in the dehydrobromination step: 20 ml of acetone plus 10 ml of DMF.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for preparing a 4,6-dien-3-one steroid comprising the steps of: reacting a steroid enolic ether having partial structural formula (I) at the 3,4,5,6-position of rings A and B thereof:

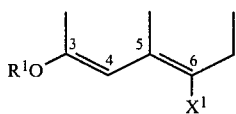
(I)

wherein $X^1$ is hydrogen, fluorine, chlorine or bromine and $R^1$ is an alkyl having 1 to 3 carbon atoms, with a halogenating agent capable of providing a positive bromine ion to brominate the ether into a 6-bromosteroid having partial structural formula (II) at the same position:

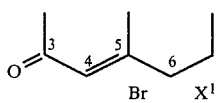
(II)

wherein $X^1$ is as defined above and one of $X^1$ and Br is in the α-configuration and the other is in the β-configuration, and reacting the reaction mixture from the brominating step directly with a lithium halide and an inorganic carbonate to effect dehydrobromination and to give a 4,6-dien-3-one steroid having partial structural formula (III) at the same position:

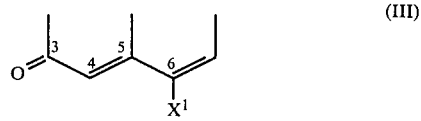
(III)

wherein $X^1$ is as defined above, the improvement comprising conducting the bromination step in a water-containing organic solvent which is substantially free from acetic acid and sodium acetate and conducting the dehydrobromination step in a medium which contains dimethylformamide or N-methylpyrrolidone and 1 to 9% by volume of water.

2. The process of claim 1, wherein $X^1$ is chlorine.

3. The process of claim 1, wherein said halogenating agent is N-bromosuccinimide.

4. The process of claim 1, wherein said lithium halide is lithium bromide and said inorganic carbonate is lithium carbonate.

5. The process of claim 1, wherein said dehydrobromination reaction is carried out in dimethylformamide.

6. The process of claim 1, wherein said organic solvent in the bromination step is selected from the group consisting of aliphatic ketones, cyclic ethers, dimethylformamide and dimethyl sulfoxide.

7. The process of claim 6, wherein said organic solvent is acetone or tetrahydrofuran.

8. The process of claim 1, wherein the volume of water used is 2 to 5%.

* * * * *